United States Patent
Neumann

(10) Patent No.: US 11,355,229 B1
(45) Date of Patent: Jun. 7, 2022

(54) SYSTEM AND METHOD FOR GENERATING AN OCULAR DYSFUNCTION NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 0 days.

(21) Appl. No.: 17/136,192

(22) Filed: Dec. 29, 2020

(51) Int. Cl.
| | |
|---|---|
| *G16H 20/60* | (2018.01) |
| *G16H 10/60* | (2018.01) |
| *G16H 50/70* | (2018.01) |
| *G06N 20/00* | (2019.01) |
| *G16H 50/20* | (2018.01) |
| *A61B 3/10* | (2006.01) |

(52) U.S. Cl.
CPC ............ *G16H 20/60* (2018.01); *G06N 20/00* (2019.01); *G16H 10/60* (2018.01); *G16H 50/20* (2018.01); *G16H 50/70* (2018.01); *A61B 3/10* (2013.01)

(58) Field of Classification Search
CPC .. G06Q 50/22–24; G16H 20/60; G06N 20/00; A61B 3/10
See application file for complete search history.

(56) References Cited

U.S. PATENT DOCUMENTS

| | | | |
|---|---|---|---|
| 7,074,183 B2 | 7/2006 | Castellanos | |
| 7,970,620 B2 | 6/2011 | Brown | |
| 8,226,414 B2 | 7/2012 | Bodin | |
| 8,560,336 B2 | 10/2013 | Schwarzberg | |

(Continued)

FOREIGN PATENT DOCUMENTS

| | | | | |
|---|---|---|---|---|
| CN | 1902325 A | * | 1/2007 | ............ G16H 10/20 |
| RU | 2691145 C2 | | 6/2019 | |

(Continued)

OTHER PUBLICATIONS

Shinn et al. Fecal Bacteria as Biomarkers for Predicting Food Intake in Healthy Adults. The Journal of Nutrition, vol. 151, Issue 2, Feb. 2021, p. 423-433, https://doi.org/10.1093/jn/nxaa285 (Year: 2020).*

(Continued)

*Primary Examiner* — Jason S Tiedeman
*Assistant Examiner* — Emily Huynh
(74) *Attorney, Agent, or Firm* — Caldwell Intellectual Property Law; Katherine Rubino

(57) ABSTRACT

A system and method for generating an ocular dysfunction nourishment program comprises a computing device configured to receive at least an ocular attribute datum as a function of a user visual system, generate at least an ocular profile as a function of the at least an ocular attribute datum, wherein generating comprises receiving an ocular utopia as a function of an ocular guideline, and generating the at least an ocular profile as a function of the at least an ocular attribute datum and the ocular utopia using an ocular machine-learning model, identify at least an edible as a (Continued)

function of the at least an ocular profile, and develop a nourishment program of a plurality of nourishment programs as a function of the edible and a profile outcome using a nourishment machine-learning model.

14 Claims, 7 Drawing Sheets

(56) References Cited

U.S. PATENT DOCUMENTS

| | | |
|---|---|---|
| 8,684,922 B2 | 4/2014 | Tran |
| 10,373,522 B2 | 8/2019 | Byron |
| 2002/0046060 A1 | 4/2002 | Hoskyns |
| 2006/0074279 A1 | 4/2006 | Brover |
| 2006/0199155 A1 | 9/2006 | Mosher |
| 2009/0307179 A1 | 12/2009 | Colby |
| 2010/0042438 A1 | 2/2010 | Moore |
| 2010/0070455 A1 | 3/2010 | Halperin |
| 2010/0136508 A1 | 6/2010 | Zekhtser |
| 2013/0261183 A1 | 10/2013 | Bhagat |
| 2015/0161355 A1 | 6/2015 | Karra |
| 2015/0356885 A1 | 12/2015 | Chen |
| 2016/0225284 A1 | 8/2016 | Schoen |
| 2018/0160894 A1* | 6/2018 | Gupta .................. A61B 5/4842 |
| 2018/0240359 A1* | 8/2018 | Hujsak .................. G06N 5/022 |
| 2018/0308389 A1 | 10/2018 | Moser |
| 2019/0073601 A1* | 3/2019 | Alkan .................... G06N 20/00 |
| 2019/0074080 A1 | 3/2019 | Appelbaum |
| 2019/0110753 A1* | 4/2019 | Zhang .................... G16H 50/20 |
| 2019/0221303 A1 | 7/2019 | Bennett |
| 2019/0251861 A1 | 8/2019 | Wolf |
| 2020/0138362 A1 | 5/2020 | Koumpan |
| 2020/0321116 A1* | 10/2020 | Neumann ............. G16H 20/10 |
| 2020/0405148 A1* | 12/2020 | Tran ..................... A61B 3/0016 |
| 2021/0007670 A1* | 1/2021 | Lamrani ................ G16H 10/40 |
| 2021/0090694 A1* | 3/2021 | Colley .................. G16H 50/70 |

FOREIGN PATENT DOCUMENTS

| | | |
|---|---|---|
| WO | 2014015378 A1 | 1/2014 |
| WO | 2019054737 A1 | 3/2019 |
| WO | 2019110412 A1 | 6/2019 |
| WO | 2019229753 A1 | 12/2019 |

OTHER PUBLICATIONS

Reference Notes: Clinical Nutrition vol. 37 Issue: 1 pp. 254-261 Published: Feb. 2018 DOI: 10.1016/j.clnu.2016.12.018 Title: Interaction between a variant of CDKN2A/B-gene with lifestyle factors in determining dyslipidemia and estimated cardiovascular risk: A step toward personalized nutrition Date: Feb. 2018; By: Mehramiz, Mehrane.

Reference Notes: Advances in Nutrition vol. 11 Issue: 1 pp. 25-34 Published: Jan. 2020 DOI: 10.1093/advances/nmz086 Title: Perspective: Guiding Principles for the Implementation of Personalized Nutrition Approaches That Benefit Health and Function Date: Jan. 2020; By: Adams, Sean H.

Reference Notes: Scientific Reports vol. 8 Article No. 14685 Published: Oct. 2, 2018 DOI: 10.1038/s41598-018-33008-7 Title: Longitudinal analysis of biomarker data from a personalized nutrition platform in healthy subjects Date: Oct. 2, 2018 By: Westerman, Kenneth.

* cited by examiner

US 11,355,229 B1

SYSTEM AND METHOD FOR GENERATING AN OCULAR DYSFUNCTION NOURISHMENT PROGRAM

FIELD OF THE INVENTION

The present invention generally relates to the field of artificial intelligence. In particular, the present invention is directed to a system and method for generating an ocular dysfunction nourishment program.

BACKGROUND

Current edible suggestion systems do not account for ocular measurements of an individual. This leads to inefficiency of an edible suggestion system and a poor nutrition plan for the individual. This is further complicated by a lack of uniformity of nutritional plans, which results in dissatisfaction of individuals.

SUMMARY OF THE DISCLOSURE

In an aspect a system for generating an ocular dysfunction nourishment program comprises a computing device, the computing device configured to receive at least an ocular attribute datum as a function of a user visual system, generate at least an ocular profile as a function of the at least an ocular attribute datum, wherein generating comprises receiving an ocular utopia as a function of an ocular guideline, and generating the at least an ocular profile as a function of the at least an ocular attribute datum and the ocular utopia using an ocular machine-learning model, identify at least an edible as a function of the at least an ocular profile, and develop a nourishment program of a plurality of nourishment programs as a function of the edible and a profile outcome using a nourishment machine-learning model.

In another aspect a method for generating an ocular dysfunction nourishment program comprises receiving, by a computing device, at least an ocular attribute datum as a function of a user visual system, generating, by the computing device, at least an ocular profile as a function of the at least an ocular attribute datum, wherein generating comprises receiving an ocular utopia as a function of an ocular guideline, and generating the at least an ocular profile as a function of the at least an ocular attribute datum and the ocular utopia using an ocular machine-learning model, identifying, by the computing device, at least an edible as a function of the at least an ocular profile, and developing, by the computing device, a nourishment program of a plurality of nourishment programs as a function of the edible and a profile outcome using a nourishment machine-learning model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating an ocular dysfunction nourishment program. In an embodiment, the disclosure may receive at least an ocular attribute datum as a function of a user visual system. Aspects of the present disclosure can be used to generate at least an ocular profile as a function of the ocular attribute datum. Aspects of the present disclosure can also be used to identify at least an edible as a function of the ocular profile. This is so, at least in part, because the edible is identified as a function of a nourishment composition using an edible machine-learning model. Aspects of the present disclosure allow for developing a nourishment program. Exemplary embodiments illustrating aspects of the present disclosure are described below in the context of several specific examples.

Figure 1:
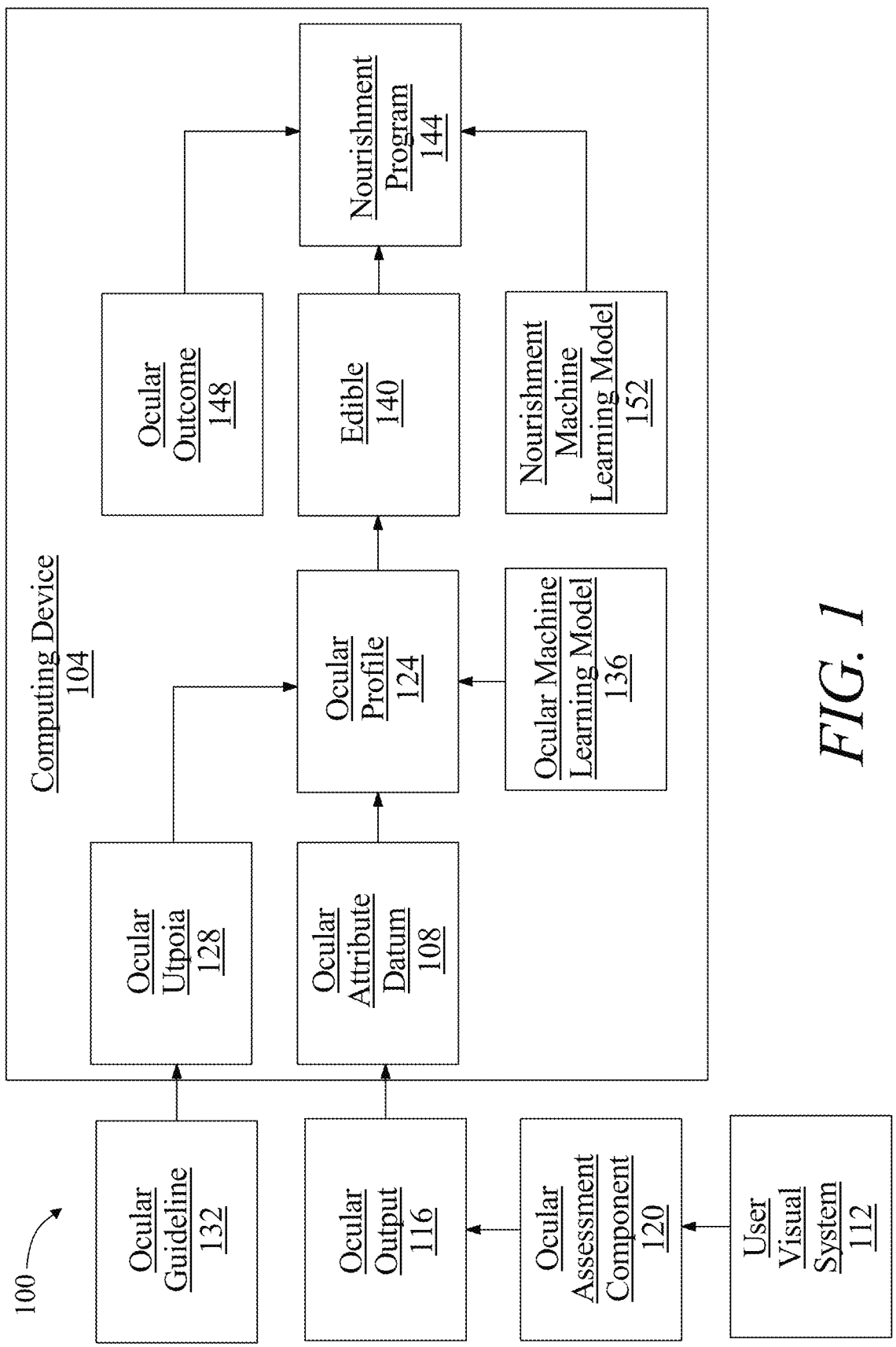
FIG. 1 is a block diagram illustrating an exemplary embodiment of a system for generating an ocular dysfunction nourishment program.

Referring now to FIG. 1, an exemplary embodiment of a system 100 for generating an ocular dysfunction nourishment program is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 receives at least an ocular attribute datum 108 as a function of a user visual system 112. As used in this disclosure "ocular attribute datum" is datum that represents a health status of a user's visual system. Ocular attribute datum 108 may include a biological sample. As used in this disclosure "biological sample" is one or more biological specimens collected from an individual. Biological sample may include, without limitation, exhalate, blood, sputum, urine, saliva, feces, semen, and other bodily fluids, as well as tissue. Ocular attribute datum 108 may relate to one or more biomarkers, wherein biomarkers are molecules and/or chemicals that at least identify the health status of a user's visual system. As a non-limiting example biomarkers may include, DNA methylation of miRNAs, COL8A1, COL8A2, Guttae formation, TGF-B1p CLU, NOX4, CDKN2A, ETS1, ARHGAP18, Gln455Lys, Leu450Trp, TCF4, TCF8, E2-2, LOXHD1, SLC4A11, FCD2, FCD3, FCD4, sACE, KL-6, Chitotriosidase, ACE, Lysozyme, and the like thereof. As used in this disclosure "user visual system" is the sensory system of an individual comprising the eye and central nervous system that allows an individual to achieve a sense of sight. As a non-limiting example user visual system may include an individual's eye, retina, optic nerve, optic tract, lateral geniculate nucleus, visual cortex, visual association cortex, and the like thereof. Computing device 104 receives ocular attribute datum 108 as a function of an ocular output 116. As used in this disclosure, an "ocular output" is an output datum of visual analysis information that is obtained from one or more ocular assessment components. As a non-limiting example ocular output may include a signal transmission of 100 ms from the lateral geniculate nucleus to the visual cortex of the brain. Ocular output 116 is obtained as a function of an ocular assessment component 120. As used in this disclosure "ocular assessment component" is a component that relates to and/or represents an element associated with the status of an individual's visual system as described in detail below, reference to FIG. 4. Ocular assessment component 120 may include one or more ocular screening tests, photokeratoscopy exams, videokeratography exams, respiratory function exams, and the like thereof. As a non-limiting example ocular assessment component may include an optical coherence tomography, retinal photography, fundus autofluorescence, external photography, corneal topography, and the like thereof. As a further non-limiting example, ocular assessment component 120 may collect, store, and/or calculate one or more lights, voltages, currents, sounds, chemicals, pressures, and the like thereof that are associated with an user visual system 112.

Still referring to FIG. 1, computing device 104 may obtain ocular attribute datum 108 as a function of an ocular assessment. As used in this disclosure "ocular assessment" is an assessment of user visual system 112 by an informed advisor. As a non-limiting example, ocular assessment may include assessing an individual's visual capability, cranial nerves, motor function, sensory function, pupillary response, reflexes, vital signs, and the like thereof. As used in this disclosure "informed advisor" is an individual that is skilled in a particular area relating to the study of optometry. As a non-limiting example an informed advisor may include a medical professional who may assist and/or participate in the medical treatment of an individual's visual system. An informed advisor may include a medical doctor, nurse, physician assistant, pharmacist, yoga instructor, nutritionist, spiritual healer, meditation teacher, fitness coach, health coach, life coach, and the like.

Still referring to FIG. 1, computing device 104 generates at least an ocular profile 124 as a function of ocular attribute datum 108. As used in this disclosure "ocular profile" is a profile of the visual system health status. As a non-limiting example, ocular profile 108 may include a visual system health status of visually impaired. As a further non-limiting example, ocular profile 108 may include a visual system health status of enhance visual acuity. Computing device 104 generates ocular profile 124 by receiving an ocular utopia 128. As used in this disclosure "ocular utopia" is an ideal visual health status that an individual may have. As a non-limiting example ocular utopia may include a visual health status of 20/20 vision, wherein 20/20 vision is visual clearness and/or sharpness to identify an object from 20 feet away. As a further non-limiting example, ocular utopia may include a measure of ocular pressure, such as 15 mm Hg. As a further non-limiting example ocular utopia may include a measure of color perception, such as CIE non-classified color vision. As a further non-limiting example, ocular utopia may include a measure of field of vision, such as 70 degrees in the horizontal meridian in each eye. As a further non-limiting example ocular utopia may include a contrast sensitivity test, such as the Pelli-Robson contrast sensitivity test that measures night vision capabilities, wherein 1.2 m and/or 3.94 ft may be recommended. As a further non-limiting example ocular utopia may include a measurement of eye tracking, such as 700°/saccade, wherein a saccade is the peak angular speed of the eye. As a further non-limiting example, ocular utopia may include a measurement of retinal health, such as 1000 μm and/or 0.039 inches for a foveal thickness and 212 μm and/or 0.0083 inches for central foveal thickness. Ocular utopia 128 may be identified according to an ocular guideline 132. As used in this disclosure "ocular guideline" is a medical guideline for the measurement of visual function. As a non-limiting example ocular guideline 132 may be identified by one or more organizations that relate to, represent, and/or study visual functions in humans, such as the American Academy of Ophthalmology, American Association of Pediatric Ophthalmology and Strabismus, American Board of Ophthalmology, American College of Eye Surgeons, American Glaucoma Society, American Medical Association, American College of Physicians, and the like thereof. As a further non-limiting example, ocular guideline 132 may include an ocular utopia as a function of one or more medical research journals, such as the Lancet, New England Journal of Medicine, Science, Journal of the American Medical Association, and the like thereof.

Still referring to FIG. 1, computing device 104 generates ocular profile 124 as a function of ocular attribute datum 108 and ocular utopia 128 using an ocular machine-learning model 136. As used in this disclosure "ocular machine-learning model" is a machine-learning model to produce an ocular profile output given ocular attribute datum and ocular utopias as inputs; this is in contrast to a non-machine learning software program where the commands to be executed are determined in advance by a user and written in a programming language. Ocular machine-learning model may include one or more ocular machine-learning processes such as supervised, unsupervised, or reinforcement machine-learning processes that computing device 104 and/or a remote device may or may not use in the determination of ocular profile 124. As used in this disclosure "remote device" is an external device to computing device 104. An ocular machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train ocular machine-learning process as a function of an ocular training set. As used in this disclosure "ocular training set" is a training set that correlates an ocular attribute datum and/or ocular utopia to an ocular profile. For example, and without limitation, an ocular attribute datum of a pupillary response time of 0.4365 seconds and an ocular utopia comprising a pupillary response time of 0.3765 sec may relate to an ocular profile of reduced iris sphincter muscle contraction. The ocular training set may be received as a function of user-entered valuations of ocular attribute datum, ocular utopias, and/or ocular profiles. Computing device 104 may receive ocular training by receiving correlations of ocular attribute data and/or ocular utopias that were previously received and/or determined during a previous iteration of determining ocular profiles. The ocular training set may be received by one or more remote devices that at least correlate an ocular attribute datum and ocular utopia to an ocular profile, wherein a remote device is an external device to computing device 104, as described above. The ocular training set may be received in the form of one or more user-entered correlations of an ocular attribute datum and ocular utopia to an ocular profile. Additionally or alternatively, a user may include an informed advisor, wherein an informed advisor may include, without limitation, optometrists, ophthalmologists, opticians, family physicians, and the like thereof.

Still referring to FIG. 1, computing device 104 may receive ocular machine-learning model from the remote device that utilizes one or more ocular machine learning processes, wherein a remote device is described above in detail. For example, and without limitation, a remote device may include a computing device, external device, processor, and the like thereof. The remote device may perform the ocular machine-learning process using the ocular training set to generate ocular profile 124 and transmit the output to computing device 104. The remote device may transmit a signal, bit, datum, or parameter to computing device 104 that at least relates to ocular profile 124. Additionally or alternatively, the remote device may provide an updated machine-learning model. For example, and without limitation, an updated machine-learning model may be comprised of a firmware update, a software update, an ocular machine-learning process correction, and the like thereof. As a non-limiting example a software update may incorporate a new ocular attribute datum that relates to a modified ocular utopia. Additionally or alternatively, the updated machine learning model may be transmitted to the remote device, wherein the remote device may replace the ocular machine-learning model with the updated machine-learning model and determine the ocular profile as a function of the ocular attribute datum using the updated machine-learning model. The updated machine-learning model may be transmitted by the remote device and received by computing device 104 as a software update, firmware update, or corrected ocular machine-learning model. For example, and without limitation an ocular machine-learning model may utilize a random forest machine-learning process, wherein the updated machine-learning model may incorporate a gradient boosting machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Still referring to FIG. 1, computing device 104 may generate ocular profile 124 by determining at least an ocular vector as a function of ocular attribute datum 108. As used in this disclosure "ocular vector" is a data structure that represents one or more a quantitative values and/or measures of ocular attribute datum 108. A vector may be represented as an n-tuple of values, where n is at least one value, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes. Computing device 104 may generate a degree of variance as a function of the ocular vector and ocular utopia. As used in this disclosure "degree of variance" is a quantitative value comprising the magnitude of divergence of the ocular attribute datum from the ocular utopia. As a non-limiting example, a degree of variance may be 7 for an eye pressure ocular attribute datum of 23 mm Hg, wherein the ocular utopia is 16 mm Hg. Degree of variance may include a transgression parameter. As used in this disclosure "transgression parameter" is a parameter that identifies one or more degrees of variance that exceed a variance limit. As a non-limiting example, transgression parameter may determine that a degree of variance should not exceed 5 for a corneal topographic measurement. As a further non-limiting, transgression parameter may determine that a degree of variance should not exceed 20 for a visual acuity examination.

Still referring to FIG. 1, computing device 104 identifies at least an edible 140 as a function of ocular profile 124. As used in this disclosure an "edible" is a source of nourishment that may be consumed by a user such that the user may absorb the nutrients from the source. For example and without limitation, an edible may include legumes, plants, fungi, nuts, seeds, breads, dairy, eggs, meat, cereals, rice, seafood, desserts, dried foods, dumplings, pies, noodles, salads, stews, soups, sauces, sandwiches, and the like thereof. Computing device 104 may identify edible 140 as a function of obtaining a nourishment composition. As used in this disclosure "nourishment composition" is a list and/or compilation of all of the nutrients contained in an edible. As a non-limiting example nourishment composition may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition may be obtained as a function of an edible directory, wherein an edible directory is a database of edibles that may be identified as a function of one or more ocular profiles, as described in detail below, in reference to FIG. 3. Computing device 104 may identify edible 140 as a function of nourishment composition, ocular profile 124, and an edible machine-learning model.

Still referring to FIG. 1, computing device 104 may identify edible 140 as a function of nourishment composition, ocular profile 124, and an edible machine-learning model. As used in this disclosure "edible machine-learning model" is a machine-learning model to produce an edible output given nourishment compositions and ocular profiles as inputs; this is in contrast to a non-machine learning software program where the commands to be executed are determined in advance by a user and written in a programming language. Edible machine-learning model may include one or more edible machine-learning processes such as supervised, unsupervised, or reinforcement machine-learning processes that computing device 104 and/or a remote device may or may not use in the determination of edible 140. An edible machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train edible machine-learning process as a function of an edible training set. As used in this disclosure a "edible training set" is a training set that correlates at least nourishment composition and ocular profile to an edible. For example, and without limitation, nourishment composition of 19 g of fiber and 1 g of carbohydrates and an ocular profile damaged blood vessels in the tissue of the back of the eye as a function of diabetic retinopathy may relate to an edible of flax seeds. The edible training set may be received as a function of user-entered valuations of nourishment compositions, ocular profiles, and/or edibles. Computing device 104 may receive edible training by receiving correlations of nourishment compositions and/or ocular profiles that were previously received and/or determined during a previous iteration of determining edibles. The edible training set may be received by one or more remote devices that at least correlate a nourishment composition and ocular profile to an edible, wherein a remote device is an external device to computing device 104, as described above. The edible training set may be received in the form of one or more user-entered correlations of a nourishment composition and ocular profile to an edible. Additionally or alternatively, a user may include an informed advisor, wherein an informed advisor may include, without limitation, optometrists, ophthalmologists, opticians, family physicians, and the like thereof.

Still referring to FIG. 1, edible machine-learning model may identify edible 140 as a function of one or more classifiers. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 may receive edible machine-learning model from the remote device that utilizes one or more edible machine learning processes, wherein a remote device is described above in detail. For example, and without limitation, a remote device may include a computing device, external device, processor, and the like thereof. The remote device may perform the edible machine-learning process using the edible training set to generate edible 140 and transmit the output to computing device 104. The remote device may transmit a signal, bit, datum, or parameter to computing device 104 that at least relates to edible 140. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a new nourishment composition that relates to a modified ocular profile. Additionally or alternatively, the updated machine learning model may be transmitted to the remote device, wherein the remote device may replace the edible machine-learning model with the updated machine-learning model and determine the edible as a function of the ocular profile using the updated machine-learning model. The updated machine-learning model may be transmitted by the remote device and received by computing device 104 as a software update, firmware update, or corrected edible machine-learning model. For example, and without limitation an edible machine-learning model may utilize a Naïve Bayes machine-learning process, wherein the updated machine-learning model may incorporate a logistic regression machine-learning process. Updated machine learning model may additionally or alternatively include any machine-learning model used as an updated machine learning model as described in U.S. Nonprovisional application Ser. No. 17/106,658.

Still referring to FIG. 1, computing device 104 may identify edible 140 by determining an ocular dysfunction as a function of ocular profile 124. As used in this disclosure "ocular dysfunction" is an ailment and/or collection of ailments that impact an individual's visual system. As a non-limiting example, ocular dysfunctions may include diabetic retinopathy, blindness, sarcoidosis, refractive error, macular degeneration, cataract, glaucoma, amblyopia, strabismus, achromatopsia 2, achromatopsia 3, alkaptonuria, aniridia, bradyopsia, Cohen syndrome, Friedreich ataxia, galactosialidosis, keratoconus, morning glory syndrome, Norrie disease, Oguchi disease, retinal cone dystrophy, snowflake vitreoretinal degeneration, tangier disease, and the like thereof. Ocular dysfunction may be determined as a function of one or more dysfunction machine-learning models. As used in this disclosure "dysfunction machine-learning model" is a machine-learning model to produce a ocular dysfunction output given ocular profiles as inputs; this is in contrast to a non-machine learning software program where the commands to be executed are determined in advance by a user and written in a programming language. Dysfunction machine-learning model may include one or more dysfunction machine-learning processes such as supervised, unsupervised, or reinforcement machine-learning processes that computing device 104 and/or a remote device may or may not use in the determination of ocular dysfunction. A dysfunction machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train dysfunction machine-learning process as a function of a dysfunction training set. As used in this disclosure "dysfunction training set" is a training set that correlates at least an ocular enumeration and a visual system effect to an ocular dysfunction. As used in this disclosure "ocular enumeration" is a measurable value associated with the ocular profile. As used in this disclosure "visual system effect" is an impact and/or effect on the visual system of an individual. As a non-limiting example an ocular enumeration of 57 may be established for a visual system effect of blurred vision, wherein an ocular dysfunction of blindness may be determined. The dysfunction training set may be received as a function of user-entered valuations of ocular enumerations, visual system effects, and/or ocular dysfunctions. Computing device 104 may receive dysfunction training by receiving correlations of ocular enumerations and/or visual system effects that were previously received and/or determined during a previous iteration of determining ocular dysfunctions. The dysfunction training set may be received by one or more remote devices that at least correlate an ocular enumeration and/or visual system effect to an ocular dysfunction, wherein a remote device is an external device to computing device 104, as described above. The dysfunction training set may be received in the form of one or more user-entered correlations of an ocular enumeration and visual system effect to an ocular dysfunction. Additionally or alternatively, a user may include an informed advisor, wherein an informed advisor may include, without limitation, optometrists, ophthalmologists, opticians, family physicians, and the like thereof.

Still referring to FIG. 1, computing device 104 may receive dysfunction machine-learning model from the remote device that utilizes one or more dysfunction machine learning processes, wherein a remote device is described above in detail. For example, and without limitation, a remote device may include a computing device, external device, processor, and the like thereof. The remote device may perform the dysfunction machine-learning process using the dysfunction training set to generate ocular dysfunction and transmit the output to computing device 104. The remote device may transmit a signal, bit, datum, or parameter to computing device 104 that at least relates to ocular dysfunctions. Additionally or alternatively, the remote device may provide an updated machine-learning model. For example, and without limitation, an updated machine-learning model may be comprised of a firmware update, a software update, a dysfunction machine-learning process correction, and the like thereof. As a non-limiting example a software update may incorporate a new ocular enumeration that relates to a modified visual system effect. Additionally or alternatively, the updated machine learning model may be transmitted to the remote device, wherein the remote device may replace the dysfunction machine-learning model with the updated machine-learning model and determine the ocular dysfunction as a function of the ocular enumeration using the updated machine-learning model. The updated machine-learning model may be transmitted by the remote device and received by computing device 104 as a software update, firmware update, or corrected dysfunction machine-learning model. For example, and without limitation dysfunction machine-learning model may utilize a hierarchical clustering machine-learning process, wherein the updated machine-learning model may incorporate logistic regression machine-learning process.

Still referring to FIG. 1, computing device 104 may identify edible as a function of a likelihood parameter. As used in this disclosure "likelihood parameter" is a parameter that identifies the probability of a user to consume an edible. As a non-limiting example likelihood parameter may identify a high probability that a user will consume an edible of salmon. As a further non-limiting example likelihood parameter may identify a low probability that a user will consume an edible of asparagus. Likelihood parameter may be determined as a function of a user taste profile. As used in this disclosure "user taste profile" is a profile of a user that identifies one or more desires, preferences, wishes, and/or wants that a user has. As a non-limiting example a user taste profile may include a user's preference for beef flavor and/or soft textured edibles. Likelihood parameter may be determined as a function of an edible profile. As used in this disclosure "edible profile" is taste of an edible is the sensation of flavor perceived in the mouth and throat on contact with the edible. Edible profile may include one or more flavor variables. As used in this disclosure "flavor variable" is a variable associated with the distinctive taste of an edible, wherein a distinctive may include, without limitation sweet, bitter, sour, salty, umami, cool, and/or hot. Edible profile may be determined as a function of receiving flavor variable from a flavor directory. As used in this disclosure "flavor directory" is a database of flavors for an edible. As a non-limiting example flavor directory may include a list and/or collection of edibles that all contain umami flavor variables. As a further non-limiting example flavor directory may include a list and/or collection of edibles that all contain sour flavor variables. Likelihood parameter may alternatively or additionally include any user taste profile and/or edible profile used as a likelihood parameter as described in U.S. Nonprovisional application Ser. No. 17/032,080, filed on Sep. 25, 2020, and entitled "METHODS, SYSTEMS, AND DEVICES FOR GENERATING A REFRESHMENT INSTRUCTION SET BASED ON INDIVIDUAL PREFERENCES," the entirety of which is incorporated herein by reference.

Still referring to FIG. 1, computing device 104 develops a nourishment program 144 of a plurality of nourishment programs as a function of edible 140. As used in this disclosure "nourishment program" is a program consisting of one or more edibles that are to be consumed over a given time period, wherein a time period is a temporal measurement such as seconds, minutes, hours, days, weeks, months, years, and the like thereof. As a non-limiting example nourishment program 144 may consist of recommending hamburgers for 8 days. As a further non-limiting example nourishment program 144 may recommend tofu for a first day, milk and cookies for a second day, and artichokes for a third day. Nourishment program 144 may include one or more diet programs such as paleo, keto, vegan, vegetarian, and the like thereof. Computing device 104 develops nourishment program as a function of an profile outcome 148. As used in this disclosure "profile outcome" is an outcome that an edible may generate according to a predicted and/or purposeful plan. As a non-limiting example, profile outcome 148 may include a treatment outcome. As used in this disclosure "treatment outcome" is an intended outcome that is designed to at least reverse and/or eliminate ocular attribute datum associated with ocular profile 124 and/or ocular dysfunction. As a non-limiting example, a treatment outcome may include reversing the effects of the ocular dysfunction diabetic retinopathy. As a further non-limiting example, a treatment outcome includes reversing the ocular dysfunction of glaucoma. Profile outcome 148 may include a prevention outcome. As used in this disclosure "prevention outcome" is an intended outcome that is designed to at least prevent and/or avert ocular attribute datum associated with ocular profile 124 and/or ocular dysfunction. As a non-limiting example, a prevention outcome may include preventing the development of the ocular dysfunction of blindness.

Still referring to FIG. 1, computing device 104 develops nourishment program 144 as a function of edible 140 and profile outcome 148 using a nourishment machine-learning model 152. As used in this disclosure "nourishment machine-learning model" is a machine-learning model to produce a nourishment program output given edibles and/or profile outcomes as inputs; this is in contrast to a non-machine learning software program where the commands to be executed are determined in advance by a user and written in a programming language. Nourishment machine-learning model 152 may include one or more nourishment machine-learning processes such as supervised, unsupervised, or reinforcement machine-learning processes that computing device 104 and/or a remote device may or may not use in the development of nourishment program 144. Nourishment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nourishment machine-learning process as a function of a nourishment training set. As used in this disclosure a "nourishment training set" is a training set that correlates a profile outcome to an edible. The nourishment training set may be received as a function of user-entered edibles, profile outcomes, and/or nourishment programs. Computing device 104 may receive nourishment training by receiving correlations of profile outcomes and/or edibles that were previously received and/or determined during a previous iteration of developing nourishment programs. The nourishment training set may be received by one or more remote devices that at least correlate a profile outcome and/or edible to a nourishment program, wherein a remote device is an external device to computing device 104, as described above. The nourishment training set may be received in the form of one or more user-entered correlations of a profile outcome an edible to a nourishment program. Additionally or alternatively, a user may include an informed advisor, wherein an informed advisor may include, without limitation, optometrists, ophthalmologists, opticians, family physicians, and the like thereof.

Still referring to FIG. 1, computing device 104 may receive nourishment machine-learning model 152 from the remote device that utilizes one or more nourishment machine learning processes, wherein a remote device is described above in detail. For example, and without limitation, a remote device may include a computing device, external device, processor, and the like thereof. The remote device may perform the nourishment machine-learning process using the nourishment training set to develop nourishment program 144 and transmit the output to computing device 104. The remote device may transmit a signal, bit, datum, or parameter to computing device 104 that at least relates to nourishment program 144. Additionally or alternatively, the remote device may provide an updated machine-learning model. For example, and without limitation, an updated machine-learning model may be comprised of a firmware update, a software update, a nourishment machine-learning process correction, and the like thereof. As a non-limiting example a software update may incorporate a new profile outcome that relates to a modified edible. Additionally or alternatively, the updated machine learning model may be transmitted to the remote device, wherein the remote device may replace the nourishment machine-learning model with the updated machine-learning model and develop the nourishment program as a function of the profile outcome using the updated machine-learning model. The updated machine-learning model may be transmitted by the remote device and received by computing device 104 as a software update, firmware update, or corrected nourishment machine-learning model. For example, and without limitation nourishment machine-learning model may utilize a neural net machine-learning process, wherein the updated machine-learning model may incorporate decision tree machine-learning processes.

Figure 2:
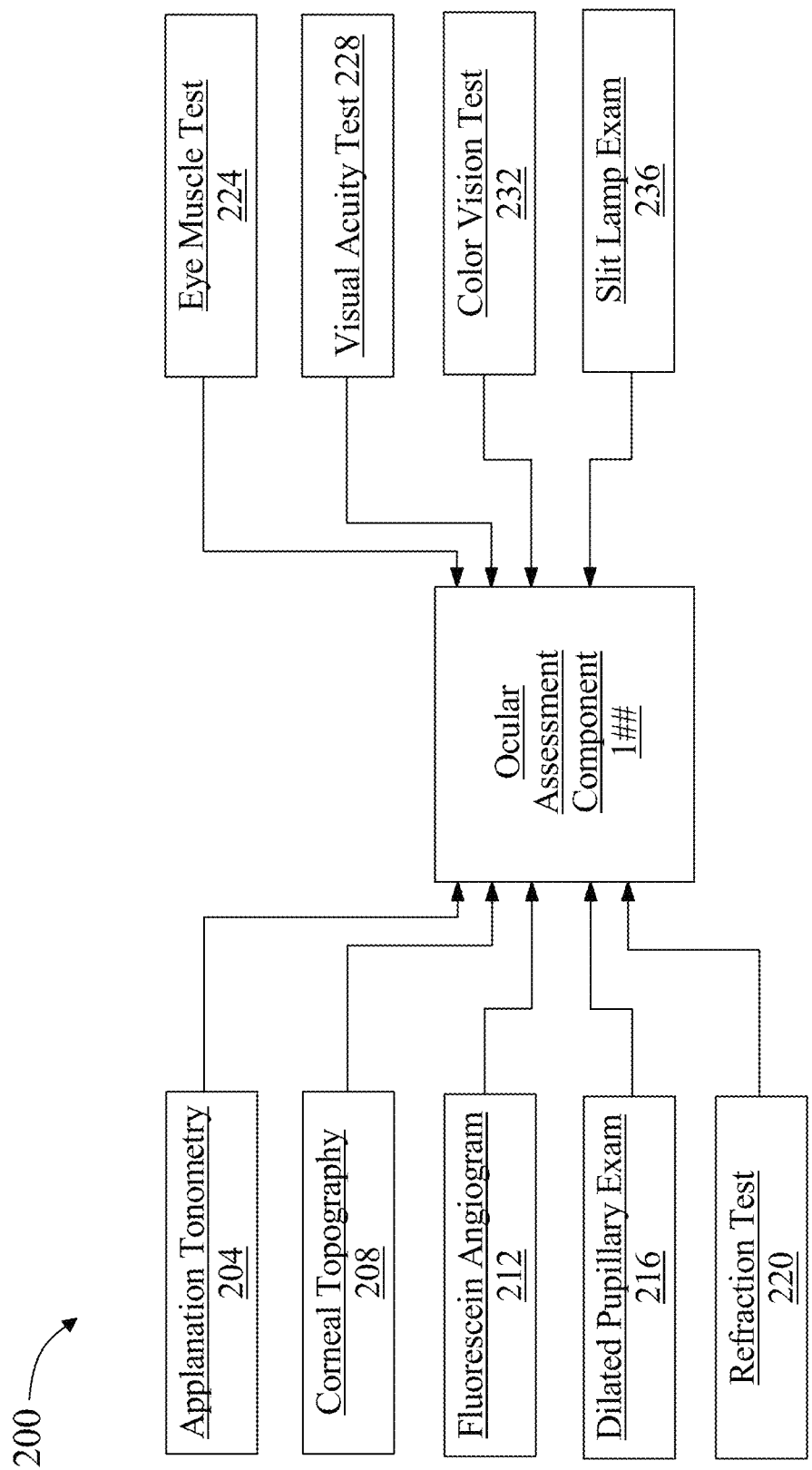
FIG. 2 is a block diagram of an exemplary embodiment of an ocular assessment component according to an embodiment of the invention.

Now referring to FIG. 2, an exemplary embodiment 200 of ocular assessment component 120 according to an embodiment of the invention is illustrated. Ocular assessment component 120 may include an applanation tonometry. As used in this disclosure "applanation tonometry" is an assessment component that measures fluid pressure in an individual's eye. As a non-limiting example, applanation tonometry 204 may include a Goldmann applanation tonometer based on the Imbert-Fick principle. Ocular assessment component 120 may include a corneal topography 208. As used in this this disclosure "corneal topography" is an assessment component that maps the surface curvature of the cornea. As a non-limiting example, corneal topography 208 may include a KISA % index and/or a keratometer. Ocular assessment component 120 may include a fluorescein angiogram 212. As used in this disclosure "fluorescein angiogram" is an assessment component that examines the circulation of the retina and choroid using a fluorescent dye and a specialized camera. As a non-limiting example fluorescein angiogram 212 may include an intravenous fluorescein angiography and/or an oral fluorescein angiography. Ocular assessment component 120 may include a dilated pupillary exam 216. As used in this disclosure "dilated pupillary exam" is assessment component that employs the use of mydriatic eye drops to dilate and/or enlarge the pupil. As a non-limiting example, may include a dilated fundus examination and/or the use of a fundus camera. Ocular assessment component 120 may include a refraction test 220. As used in this disclosure "refraction test" is an assessment component that measures the optical abnormality of the shape of the eye that fails to bring light into sharp focus on the retina. As a non-limiting example, refraction test 220 may include an objective refraction, a subjective refraction, and/or a cycloplegic refraction. Ocular assessment component 120 may include a eye muscle test 224. As used in this disclosure "eye muscle test" is an assessment component that measures the muscle function that controls the movement of the eye. As a non-limiting example, eye muscle test 224 may include measurements from one or more ocular muscles such as the medial rectus, lateral rectus, superior rectus, inferior rectus, superior oblique, inferior oblique, levator palpebrae superioris, and the like thereof. Ocular assessment component 120 may include a visual acuity test 228. As used in this disclosure "visual acuity test" is an assessment component that measure the ability to detect fine details of objects at a certain distance. As a non-limiting example visual acuity test may include 20/20 vision, 6/6 vision, 20/15 vision, 20/200 vision, and the like thereof. Ocular assessment component 120 may include a color vision test 232. As used in this disclosure "color vision test" is an assessment component that measures the color perception of an individual's visual system. For example, and without limitation, color vision test 232 may include an Ishihara plate, wherein an Ishihara plate may include one or more demonstration plates, transformation plates, vanishing plates, hidden digit, plates, diagnostic plates, and/or tracing plates. Ocular assessment component 120 may include a slit lamp exam 236. As used in this disclosure "slit lamp exam" is an assessment component that displays a high-intensity light source such that a reflection may be witnessed on the anterior segment and posterior segment of the human eye. As a non-limiting example, slit lamp exam 236 may include one or more diffuse illuminations, direct focal illuminations, specular reflections, transilluminations, retroilluminations, indirect illuminations, sclerotic scatters, and/or scattering sclero-corneal illuminations.

Figure 3:
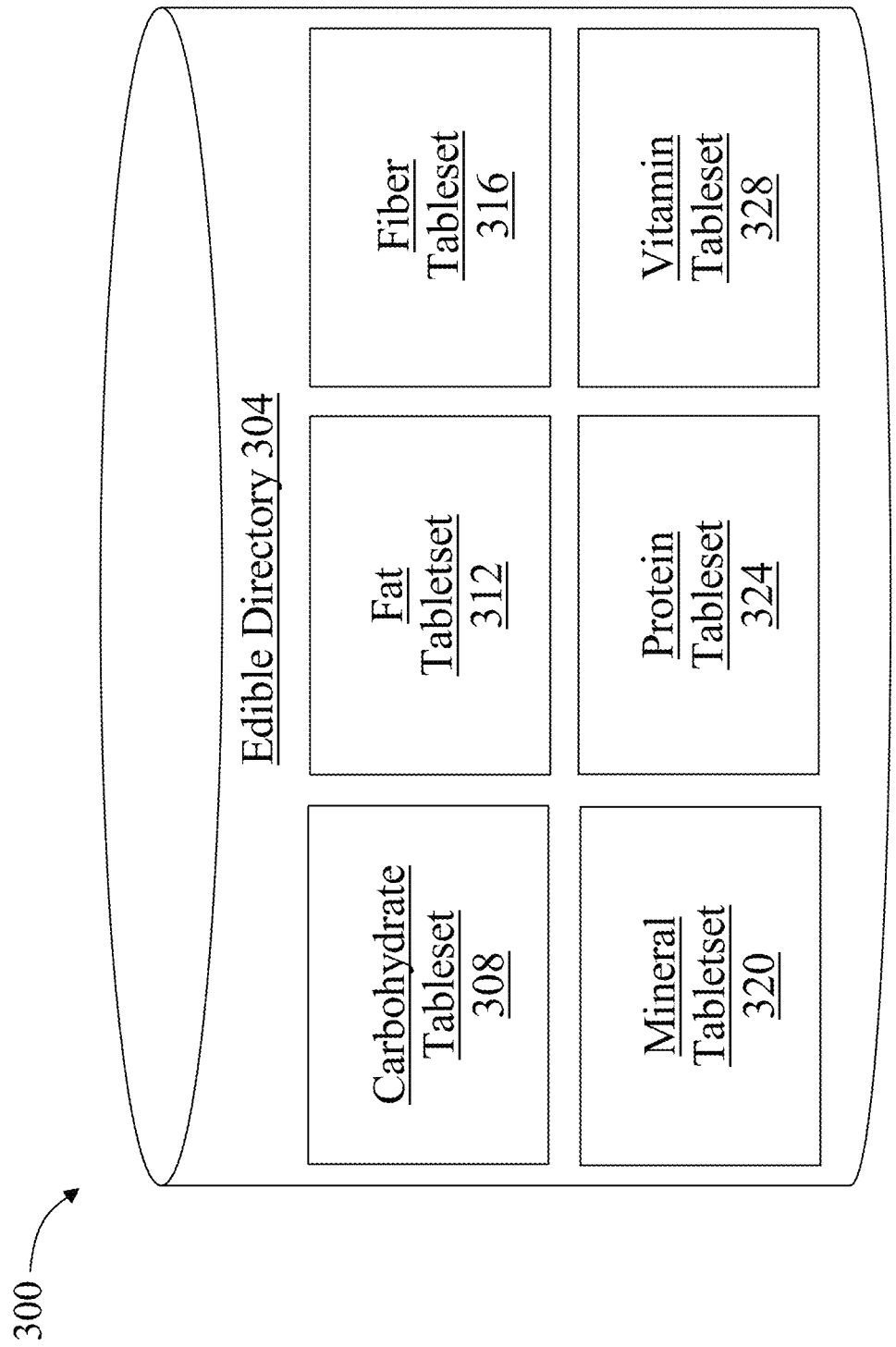
FIG. 3 is a block diagram of an exemplary embodiment of an edible directory according to an embodiment of the invention.

Now referring to FIG. 3, an exemplary embodiment 300 of an edible directory 304 according to an embodiment of the invention is illustrated. Edible directory 304 may be implemented, without limitation, as a relational databank, a key-value retrieval databank such as a NOSQL databank, or any other format or structure for use as a databank that a person skilled in the art would recognize as suitable upon review of the entirety of this disclosure. Edible directory 304 may alternatively or additionally be implemented using a distributed data storage protocol and/or data structure, such as a distributed hash table or the like. Edible directory 304 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory 304 may include a carbohydrate tableset 308. Carbohydrate tableset 308 may relate to a nourishment composition of an edible with respect to the quantity and/or type of carbohydrates in the edible. As a non-limiting example, carbohydrate tableset 308 may include monosaccharides, disaccharides, oligosaccharides, polysaccharides, and the like thereof. Edible directory 304 may include a fat tableset 312. Fat tableset 312 may relate to a nourishment composition of an edible with respect to the quantity and/or type of esterified fatty acids in the edible. Fat tableset 312 may include, without limitation, triglycerides, monoglycerides, diglycerides, phospholipids, sterols, waxes, and free fatty acids. Edible directory 304 may include a fiber tableset 316. Fiber tableset 316 may relate to a nourishment composition of an edible with respect to the quantity and/or type of fiber in the edible. As a non-limiting example, fiber tableset 316 may include soluble fiber, such as beta-glucans, raw guar gum, *psyllium*, inulin, and the like thereof as well as insoluble fiber, such as wheat bran, cellulose, lignin, and the like thereof. Edible directory 304 may include a mineral tableset 320. Mineral tableset 320 may relate to a nourishment composition of an edible with respect to the quantity and/or type of minerals in the edible. As a non-limiting example, mineral tableset 320 may include calcium, phosphorous, magnesium, sodium, potassium, chloride, sulfur, iron, manganese, copper, iodine, zing, cobalt, fluoride, selenium, and the like thereof. Edible directory 304 may include a protein tableset 324. Protein tableset 324 may relate to a nourishment composition of an edible with respect to the quantity and/or type of proteins in the edible. As a non-limiting example, protein tableset 324 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Edible directory 304 may include a vitamin tableset 328. Vitamin tableset 328 may relate to a nourishment composition of an edible with respect to the quantity and/or type of vitamins in the edible. As a non-limiting example, vitamin tableset 328 may include vitamin A, vitamin $B_1$, vitamin $B_2$, vitamin $B_3$, vitamin Bs, vitamin $B_6$, vitamin $B_7$, vitamin $B_9$, vitamin $B_{12}$, vitamin C, vitamin D, vitamin E, vitamin K, and the like thereof.

Figure 4:
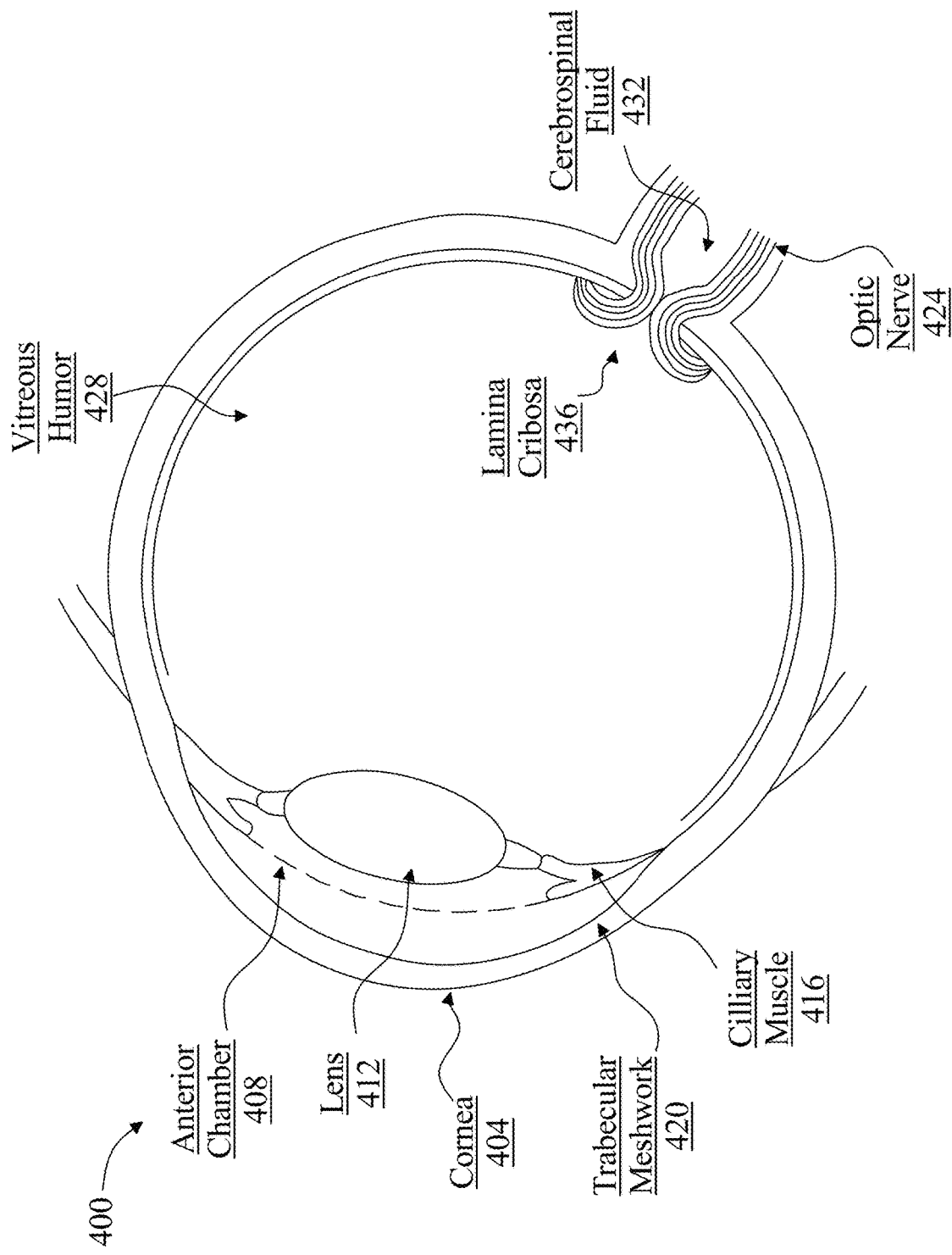
FIG. 4 is a block diagram of an exemplary embodiment of a user visual system according to an embodiment of the invention.

Now referring to FIG. 4, an exemplary embodiment of a user visual system 112 is illustrated. User visual system 112 may include a cornea 404. As used in this disclosure "cornea" is the transparent portion of the eye that covers the front portion of the eye, including the pupil, iris, and anterior chamber. As a non-limiting example cornea 404 may refract and/or bend light prior to entering user visual system 112. User visual system 112 may include an anterior chamber 408. As used in this disclosure "anterior chamber" is the aqueous humor-filled space inside of the eye between the iris and the cornea's innermost surface, the endothelium. As a non-limiting example the anterior chamber may relate to one or more ocular dysfunctions of hymphema, anterior uveitis, and/or glaucoma. User visual system 112 may include a lens 412. As used in this disclosure "lens" is a transparent biconvex structure in the eye that helps to refract light to be focused on the retina. As a non-limiting example lens 412 may include a lens capsule, lens epithelium, lens fiber, and the like thereof. User visual system 112 may include a ciliary muscle 416. As used in this disclosure "ciliary muscle" is a ring of smooth muscle in eye's middle layer that controls accommodation for viewing objects at varying distances and regulates the flow of aqueous humor into Schlemm's canal. As a nonlimiting example, ciliary muscle 416 may change the shape of the lens within the eye to alter the amount of light that may enter the eye. User visual system 112 may include a trabecular meshwork 420. As used in this disclosure "trabecular meshwork" is an area of tissue in the eye located around the base of the cornea, near the ciliary muscle, that drains the aqueous humor from the eye via the anterior chamber. As a non-limiting example, trabecular meshwork 420 may include an inner uveal meshwork, corneoscleral meshwork, juxtacanalicular tissue, and the like thereof. Use visual system may include an optic nerve 424. As used in this disclosure "optic nerve" is a cranial nerve that transmits visual information from the retina to the lateral geniculate nucleus, pretectal nucleus, and/or superior colliculus. As a non-limiting example optic nerve 424 may control one or more light reflexes and/or accommodation reflexes of the user. User visual system 112 may include a vitreous humor 428. As used in this disclosure "vitreous humor" is a clear gel that fills the space between the lens and the retina of the eyeballs of a user. As a non-limiting example vitreous humor 428 may include anatomical landmarks such as the hyaloid membrane, Berger's space, space of Erggelet, Wieger's ligament, Cloquet's canal, and/or the space of Martegiani. User visual system may include cerebrospinal fluid 432. As used in this disclosure "cerebrospinal fluid" is a clear, colorless fluid that surround optic nerve 424. As a non-limiting example, cerebrospinal fluid 432 may provide basic mechanical and immunological protection to optic nerve 424 by occupying the subarachnoid space of the optic nerve. User visual system 112 may include a lamina cribosa 436. As used in this disclosure "lamina cribosa" is a mesh-like structure that allows nerve fibers of the optic nerve to pass through the sclera of the eye. As a non-limiting example lamina cribosa 436 may maintain the pressure gradient between the inside of the eye and the surrounding tissue.

Figure 5:
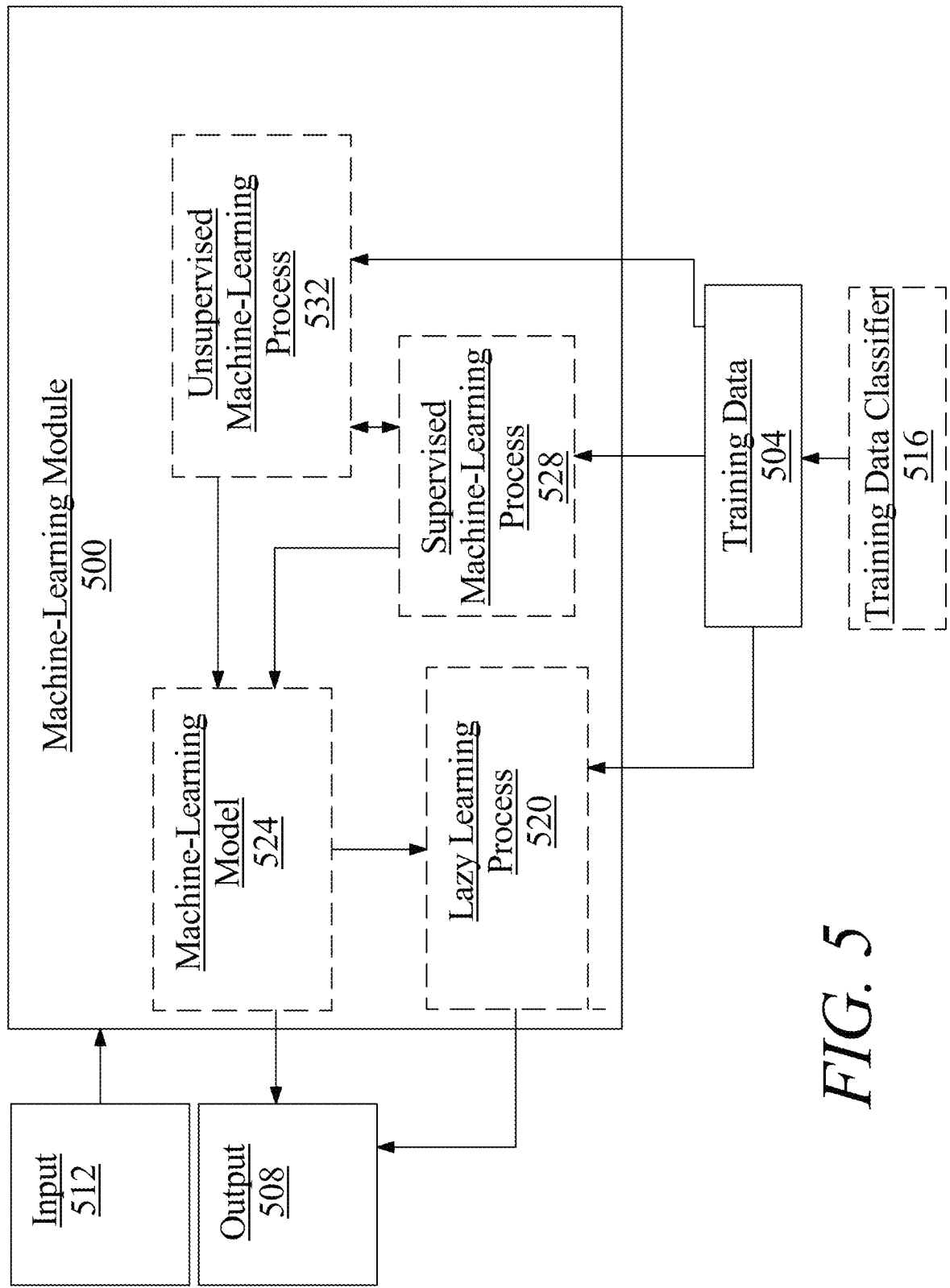
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example inputs of edibles and profile outcomes may result in nourishment program outputs.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to sub-categories of treatment or prevention profile outcomes.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include profile outcomes and/or edibles as described above as inputs, nourishment programs as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
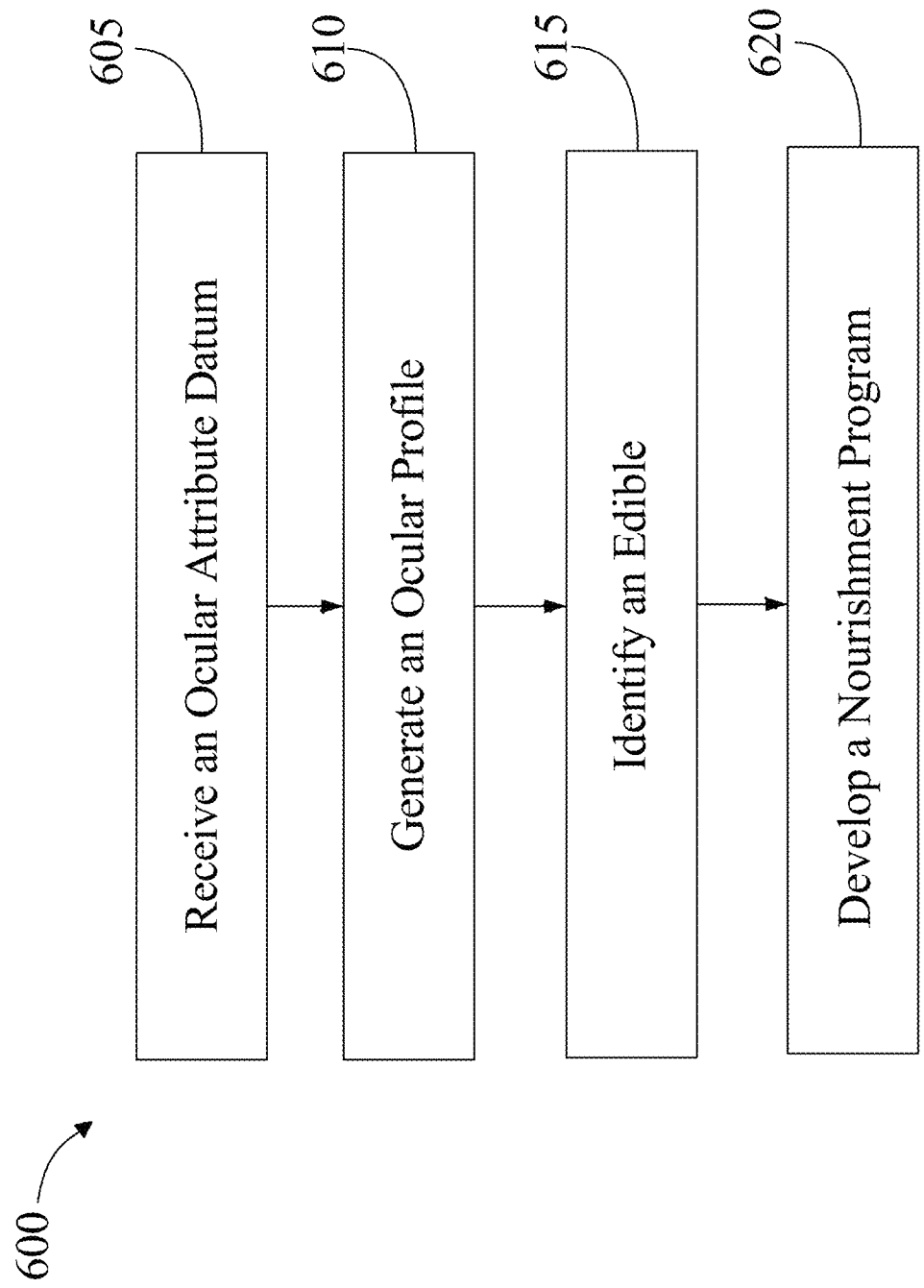
FIG. 6 is a process flow diagram illustrating an exemplary embodiment of a method of generating an ocular dysfunction nourishment program.

Now referring to FIG. 6, an exemplary embodiment of a method 600 for generating an ocular dysfunction nourishment program is illustrated. At step 605, a computing device 104 receives at least an ocular attribute datum 108 as a function of a user visual system 112. Computing device 104 includes any of the computing device 104 as described above, in reference to FIGS. 1-5. Ocular attribute datum 108 includes any of the ocular attribute datum 108 as described above, in reference to FIGS. 1-5. User visual system 112 includes any of the user visual system 112 as described above, in reference to FIGS. 1-5. Computing device 104 receives ocular attribute datum 108 by obtaining an ocular output 116 as a function of an ocular assessment component 120. Ocular output 116 includes any of the ocular output 116 as described above, in reference to FIGS. 1-5. Ocular assessment component 120 includes any of the ocular assessment component 120 as described above, in reference to FIGS. 1-5.

Still referring to FIG. 6, at step 610, computing device 104 generates at least an ocular profile 124 as a function of ocular attribute datum 108. Ocular profile 124 includes any of the ocular profile 124 as described above, in reference to FIGS. 1-5. Computing device 104 generates ocular profile 124 by receiving an ocular utopia 128 as a function of an ocular guideline 132. Ocular utopia 128 includes any of the ocular utopia 128 as described above, in reference to FIGS. 1-5. Ocular guideline 132 includes any of the ocular guideline 132 as described above, in reference to FIGS. 1-5. Computing device 104 generates ocular profile 124 as a function of the ocular attribute datum 152 and ocular utopia 128 using an ocular machine-learning model 136. Ocular machine-learning model 136 includes any of the ocular machine-learning model 136 as described above, in reference to FIGS. 1-5.

Still referring to FIG. 6, at step 615, computing device 104 identifies at least an edible 140 as a function of ocular profile 124. Edible 140 includes any of the edible 140 as described above, in reference to FIGS. 1-5.

Still referring to FIG. 6, at step 620, computing device 104, develops a nourishment program 144 of a plurality of nourishment programs as a function of edible 140 and a profile outcome 148 using a nourishment machine-learning model 152. Nourishment program 144 includes any of the nourishment program 144 as described above, in reference to FIGS. 1-5. Profile outcome 148 includes any of the profile outcome 148 as described above, in reference to FIGS. 1-5. Nourishment machine-learning model 152 includes any of the nourishment machine-learning model 152 as described above, in reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
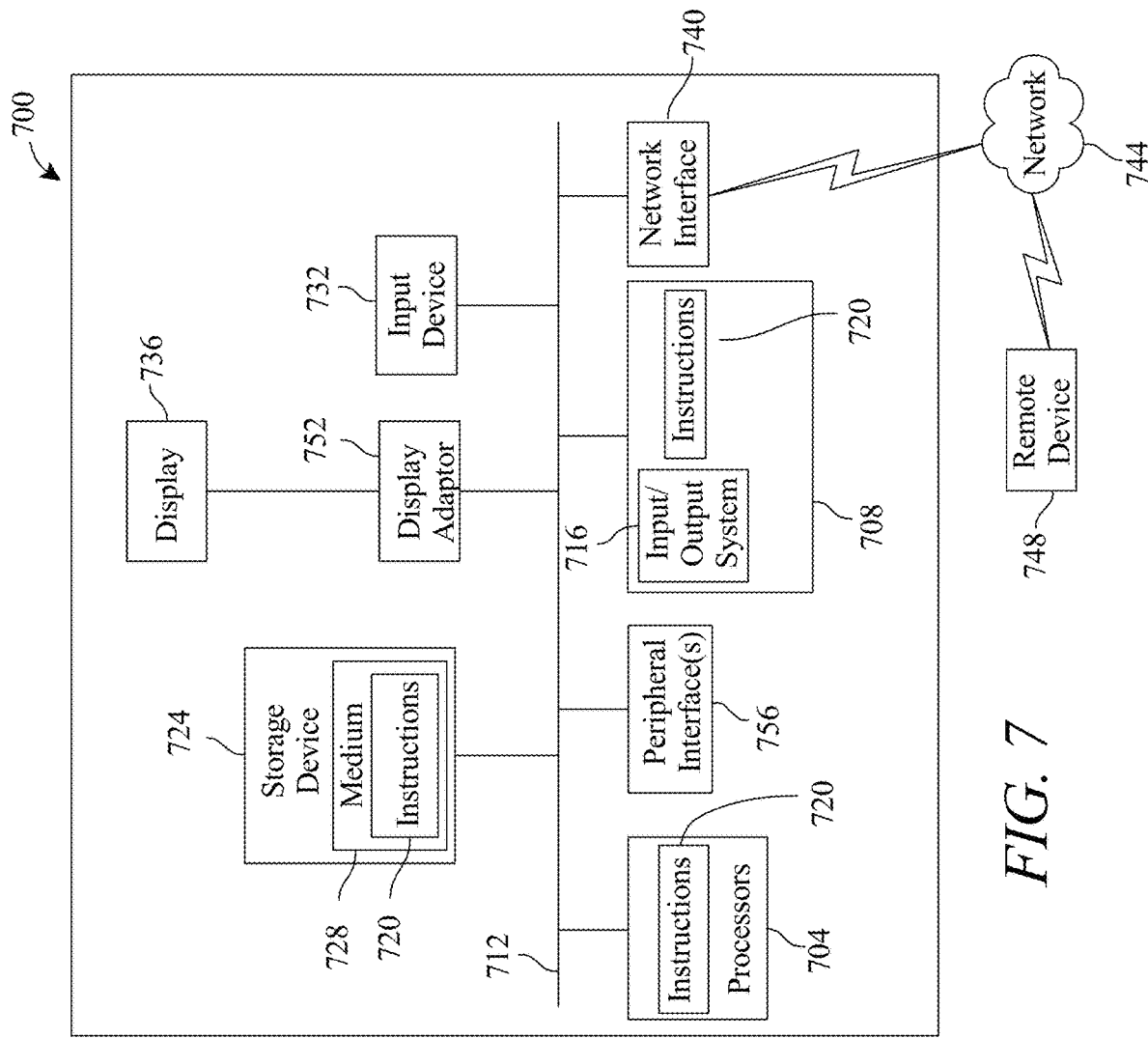
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating an ocular dysfunction nourishment program, the system comprising: a computing device, the computing device configured to:
   receive at least an ocular attribute datum as a function of a user visual system;
   generate at least an ocular profile as a function of the at least an ocular attribute datum, wherein generating comprises:
      receiving an ocular utopia as a function of an ocular guideline; and
      generating the at least an ocular profile as a function of the at least an ocular attribute datum and the ocular utopia using an ocular machine-learning model, wherein generating the ocular machine-learning model further comprises:
         training the ocular machine-learning model by training data that contains a plurality of ocular attribute datum and ocular utopia as inputs correlated to a plurality of ocular profiles as outputs; and
         generating the ocular machine-learning model wherein the ocular machine-learning model receives the ocular attribute datum and the ocular utopia as inputs and outputs the at least an ocular profile;
   identify at least an edible, wherein identifying comprises:
      determining an edible profile identifying a likelihood parameter, wherein the likelihood parameter relates a user taste profile to the edible profile; and identifying the at least an edible as a function of the likelihood parameter;

develop a nourishment program from a plurality of nourishment programs using a nourishment machine-learning model, wherein the nourishment machine-learning model further comprises:
   training the nourishment machine-learning model by training data that contains a plurality of edibles and profile outcomes as inputs correlated to a plurality of nourishment programs as outputs; and
   outputting the nourishment program as a function of training the nourishment machine-learning model, wherein the nourishment machine-learning model receives the edible and the profile outcomes as inputs and outputs the nourishment program, and wherein the nourishment machine-learning model is optimized by using a scoring function, wherein the scoring function is a loss function.

2. The system of claim 1, wherein the at least an ocular attribute datum includes a biomarker.

3. The system of claim 1, wherein generating the at least an ocular profile further comprises:
   determining at least an ocular vector as a function of the at least an ocular attribute datum; and
   generating a degree of variance as a function of the at least an ocular vector and the ocular utopia.

4. The system of claim 3, wherein the degree of variance includes a transgression parameter.

5. The system of claim 1, wherein determining the edible profile further comprises:
   receiving a flavor variable from a flavor directory; and
   determining the edible profile as a function of the flavor variable.

6. The system of claim 1, wherein the profile outcome includes a treatment outcome.

7. The system of claim 1, wherein the profile outcome includes a prevention outcome.

8. A method for generating an ocular dysfunction nourishment program, the method comprising:
   receiving, by a computing device, at least an ocular attribute datum as a function of a user visual system;
   generating, by the computing device, at least an ocular profile as a function of the at least an ocular attribute datum, wherein generating comprises:
      receiving an ocular utopia as a function of an ocular guideline; and
      generating the at least an ocular profile as a function of the at least an ocular attribute datum and the ocular utopia using an ocular machine-learning model, wherein generating the ocular machine-learning model further comprises:
         training the ocular machine-learning model by training data that contains a plurality of ocular attribute datum and ocular utopia as inputs correlated to a plurality of ocular profiles as outputs; and
         generating the ocular machine-learning model wherein the ocular machine-learning model receives the ocular attribute datum and the ocular utopia as inputs and outputs the at least an ocular profile;
   identifying, by the computing device, at least an edible, wherein identifying comprises:
      determining an edible profile identifying a likelihood parameter, wherein the likelihood parameter relates a user taste profile to the edible profile; and
      identifying the at least an edible as a function of the likelihood parameter; and
   developing, by the computing device, a nourishment program from a plurality of nourishment programs using a nourishment machine-learning model, wherein the nourishment machine-learning model further comprises:
      training the nourishment machine-learning model by training data that contains a plurality of edibles and profile outcomes as inputs correlated to a plurality of nourishment programs as outputs; and
      outputting the nourishment program as a function of training the nourishment machine-learning model, wherein the nourishment machine-learning model receives the edible and the profile outcomes as inputs and outputs the nourishment program, and wherein the nourishment machine-learning model is optimized by using a scoring function, wherein the scoring function is a loss function.

9. The method of claim 8, wherein the at least an ocular attribute datum includes a biomarker.

10. The method of claim 8, wherein generating the at least an ocular profile further comprises:
   determining at least an ocular vector as a function of the at least an ocular attribute datum; and
   generating a degree of variance as a function of the at least an ocular vector and the ocular utopia.

11. The method of claim 10, wherein the degree of variance includes a transgression parameter.

12. The method of claim 8, wherein determining the edible profile further comprises:
   receiving a flavor variable from a flavor directory; and
   determining the edible profile as a function of the flavor variable.

13. The method of claim 8, wherein the profile outcome includes a treatment outcome.

14. The method of claim 8, wherein the profile outcome includes a prevention outcome.

* * * * *